US005810762A

United States Patent [19]

Hofmann

[11] Patent Number: 5,810,762

[45] Date of Patent: Sep. 22, 1998

[54] ELECTROPORATION SYSTEM WITH VOLTAGE CONTROL FEEDBACK FOR CLINICAL APPLICATIONS

[75] Inventor: Gunter A. Hofmann, San Diego, Calif.

[73] Assignee: Genetronics, Inc., San Diego, Calif.

[21] Appl. No.: 930,168

[22] PCT Filed: Apr. 10, 1995

[86] PCT No.: PCT/US95/04384

§ 371 Date: Oct. 8, 1997

§ 102(e) Date: Oct. 8, 1997

[87] PCT Pub. No.: WO96/32155

PCT Pub. Date: Oct. 17, 1996

[51] Int. Cl.[6] .......... A61N 1/30

[52] U.S. Cl. .......... 604/20; 604/49; 607/145

[58] Field of Search .......... 604/20, 19, 49; 607/145, 115, 116; 606/48, 50, 51

[56] References Cited

U.S. PATENT DOCUMENTS

| | | | |
|---|---|---|---|
| 5,389,069 | 2/1995 | Weaver | 604/21 |
| 5,439,440 | 8/1995 | Hofmann | 604/20 |
| 5,507,724 | 4/1996 | Hofmann et al. | 604/53 |
| 5,688,233 | 11/1997 | Hofmann et al. | 604/20 |
| B1 5,019,034 | 8/1995 | Weaver et al. | 604/20 |

*Primary Examiner*—Scott M. Getzow
*Attorney, Agent, or Firm*—Baker & Maxham

[57] ABSTRACT

An electrode apparatus for the application of electroporation to a portion of the body of a patient, comprising a support member, a pair of electrodes adjustably mounted on the support member for movement toward and away from one another for positioning on opposite sides of a body portion to be electroporated, a sensing element for sensing a distance between the electrodes and generating a distance signal proportionate to the distance between the electrodes, and means responsive to said distance signal for applying pulses of high amplitude electric energy to the electrodes proportionate to the distance between the electrodes.

20 Claims, 6 Drawing Sheets

ELECTROPORATION SYSTEM WITH VOLTAGE CONTROL FEEDBACK FOR CLINICAL APPLICATIONS

TECHNICAL FIELD

The present invention relates to the treatment of ailments in humans and other manmmals, and more particularly, to an improved apparatus for the application of controlled electric fields for delivering pharmaceutical compounds and genes into live cells of a patient by electroporation.

BACKGROUND ART

Electroporation has recently been suggested as one approach to the treatment of certain diseases such as cancer. For example, in the treatment of certain types of cancer with chemotherapy it is necessary to use a high enough dose of a drug to kill the cancer cells without killing an unacceptable high number of normal cells. If the chemotherapy drug could be inserted directly inside the cancer cells, this objective could be achieved. However, some of the best anti-cancer drugs, for example, bleomycin, normally cannot penetrate the membranes of certain cancer cells.

Similarly, certain diseases could be treated by introducing desired genes into the specific cells of the patient. At present, most gene therapy experiments have utilized retroviruses as the carrier of the gene into the cells. When a retrovirus enters a target cell, it integrates essentially randomly in the genome and thus has the potential for introducing mutational damage by the mere fact of its insertion. If the virus integrates adjacent to an oncogene, malignant transformation of the target cell can result.

In the 1970's it was discovered that electric fields could be used to create pores in cells without causing permanent damage to them. This discovery made possible the insertion of large molecules into cell cytoplasm. It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells. There they can modify the genome of the cell.

One therapeutic application of electroporation is for cancer treatment. Experiments on laboratory mammals have been carried out and reported as follows: Okino, M., E. Kensuke, 1990. The Effects of a Single High Voltage Electrical Stimulation with an Anticancer Drug on in vivo Growing Malignant Tumors. Jap. Journal of Surgery. 20: 197–204. Mir, L. M., S. Orlowski, J. Belehradek Jr., and C. Paoletti. 1991. Electrochemotherapy Potentiation of Antitumor Effect of Bleomycin by Local Electric Pulses. Eur. J. Cancer. 27: 68–72. Clinical trials have been conducted and reported by Mir, L. M., M. Belehradek, C. Domenge, S. Orlowski, B. Poddevin, et al. 1991. Electrochemotherapy, a novel antitumor treatment: first clinical trial. C.R. Acad. Sci. Paris. 313: 613–618.

This treatment is carried out by infusing an anticancer drug directly into the tumor and applying an electric field to the tumor between a pair of electrodes. The field strength must be adjusted reasonably accurately so that electroporation of the cells of the tumor occurs without damage to any normal or healthy cells. This can normally be easily carried out with external tumors by applying the electrodes to opposite sides of the tumor so that the electric field is between the electrodes. The distance d between the electrodes can then be measured and a suitable voltage according to the formula $E=V/d$ can then be applied to the electrodes.

When internal tumors are to be treated, it is not easy to properly locate electrodes and measure the distance between them. It would be desirable to have an apparatus that provides information as to the distance between electrodes in a therapeutic apparatus.

DISCLOSURE OF INVENTION

Accordingly, it is the primary object of the present invention to provide an improved apparatus that provides information as to the distance between electrodes in a therapeutic apparatus.

It is another principal object of the present invention to provide an improved apparatus that provides information feedback of the distance between electrodes in an electroporation therapeutic apparatus for medicated, in vivo, intra cellular drug and gene therapy.

In accordance with a primary aspect of the present invention an electrode apparatus for the application of electroporation to a portion of the body of a patient, comprises a support member, a pair of electrodes adjustably mounted on said support member for movement toward and away from one another, sensing means for sensing a distance between said electrodes and generating a distance signal proportionate to the distance between said electrodes, and means including a signal generator responsive to said distance signal for applying an electric signal to the electrodes proportionate to the distance between said electrodes for generating an electric field of a predetermined strength.

BRIEF DESCRIPTION OF DRAWING

The objects, advantages and features of this invention will be more readily appreciated from the following detailed description, when read in conjunction with the accompanying drawing, in which:

FIG. 1 illustrates an operating room showing a patient undergoing laparoscopic procedures employing the invention.

BEST MODES FOR CARRYING OUT THE INVENTION

As used herein the term "molecules" includes pharmacological agents. genes, antibodies or other proteins. One human therapeutic application of electroporation consists of infusion of an anticancer drug into a tumor and electroporation of the drug into the tumor cells by applying voltage pulses between electrodes disposed on opposite sides of the tumor, called electrochemotherapy (ECT). The present invention was devised primarily for enabling ECT such as that reported by Okino and Mir et al to be carried out on tumors inside the body. However, it may be utilized for other therapeutic applications.

Referring to FIG. 1, an operating room scene is illustrated wherein a patient is undergoing minimally invasive surgery by laparoscopic techniques. This involves the insertion of small tubes through the abdominal wall through which instruments are inserted to gain access to the abdominal cavity to perform surgery or other treatment procedures therein.

In the illustration, laparoscopic instruments 12, 14, 16 and 18 are illustrated in place. The present invention provides instruments and methods to treat such diseases as pancreatic cancer by electroporation. The invention provides electroporation forceps for use through laparoscopic technique for application to tissue within the abdominal cavity. Thus, any tumor that can be accessed through laparoscopic or similar techniques can be treated in accordance with the present invention.

Figure 2:
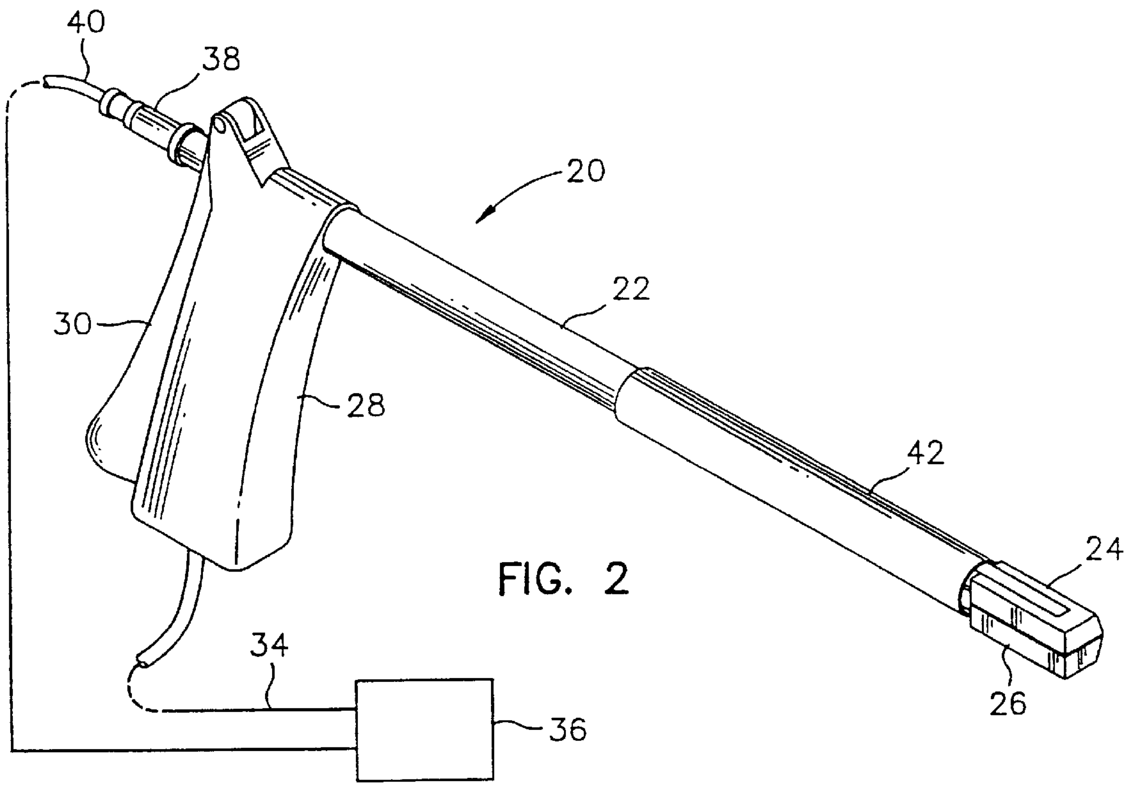
FIG. 2 illustrates a preferred embodiment of the invention for laparoscopic use in the body.
Figure 3:
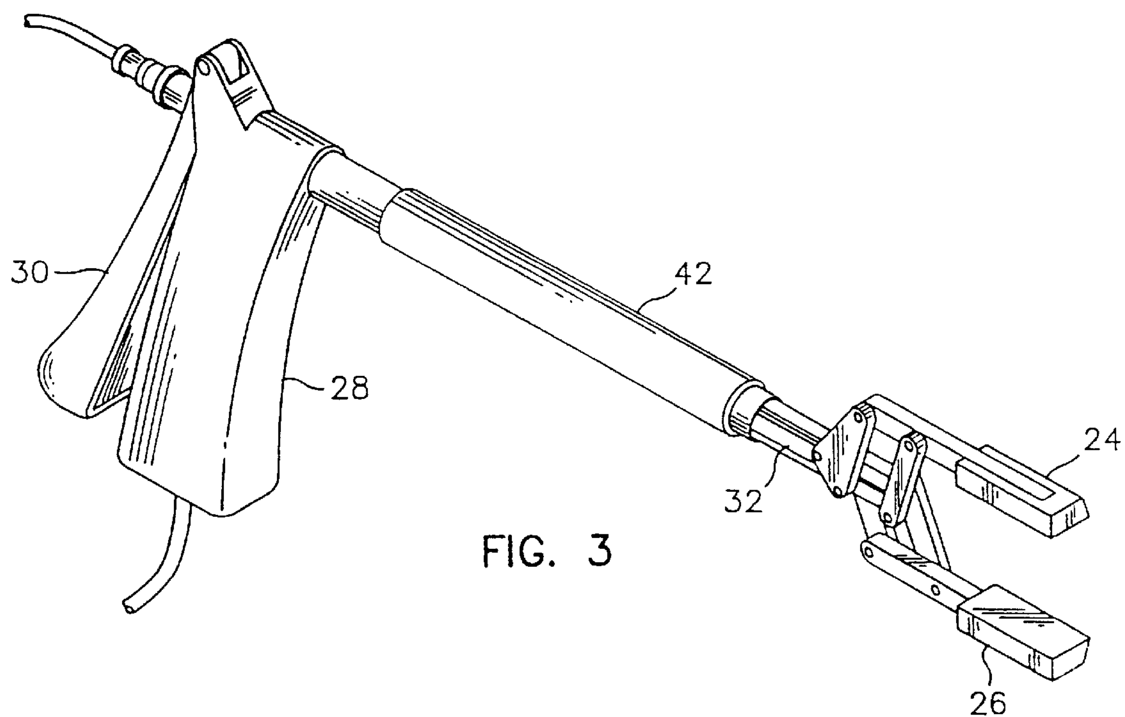
FIG. 3 is a view like FIG. 2 showing the apparatus in a different position of adjustment.

Referring to FIGS. 2 and 3, a preferred embodiment of my apparatus includes a forceps device 20 which comprises a support member 22 having a pair of electrodes 24 and 26 mounted on an insulated linkage of the distal end thereof. A pistol grip handle 28 is mounted on a proximal end of the elongated tubular support member for manipulation of same. The electrodes 24 and 26 are mounted on a moveable linkage so that the electrodes move toward and away from one another like the jaws of a clamp. A movable handle 30 is pivotally mounted at an upper end to grip 28 and connects through a moveable or actuating link 32 to the electrode links controlling the spacing between them. The electrodes 24 and 26 may be biased by spring means (not shown) acting between grip 28 and handle 30 to the open or outermost position. The electrodes 24 and 26 are connected through conductors in a cable 34 to suitable power or pulse generator 36.

A suitable sensing unit 38 senses the distance between the electrodes and generates a signal which is transmitted via conductor cable 40 to the pulse generator. The sensing unit 38 may be a device such as a linear potentiometer that provides a resistance directly proportioned to the distance between electrodes 24 and 26. A telescopic sleeve or sheath 42 covers the linkage mechanism during insertion of the conductors into the body.

The distance between the electrodes 22 and 26 is one parameter that goes into the adjustment of the voltage to obtain the optimum amplitude of the electric field to be applied. This parameter and its measure and implementation may be carried out in many ways. A mechanical indicator coupled to the applicator linkage may provide a readout indicating distance in centimeters or other units which the operator enters manually into the electrical field generating machine. A linear or rotational potentiometer connected to the linkage may provide an electrical signal which provides the readout or fed directly into the pulse generator 36.

The electrode distance may also be monitored by a change in capacitance, attenuation of light or other means which generates some form of signal such as an electric signal representative of distance between the electrodes. The signal can then provide means for activating a read-out, such as a numerical indication in centimeters or the like. The signal may also be amplified and directed to suitable control means which functions to set the voltage of a pulse generator 36 in proportion to the distance represented by the signal.

In operation, a unit as above described is inserted into a cavity of a patient via a tube 12 and the electrode jaws are opened and a selected tissue to be treated is placed and gripped between the electrode jaws. A signal proportionate to the distance between the electrodes is generated and either manually or electronically entered into the pulse generator 36 so that it generates a pulse proportional to the desired field and applies it to the electrodes. The pulse generator connected to the electrodes is then operated by a trigger switch at the unit, a foot switch, or a switch on the instrument panel for repeatedly applying pulses to the electrodes for generating electric fields of a predetermined amplitude and duration in the tissue between the electrodes.

The fields are generated by applying a predetermined electric signal to electrodes 24 and 26 of the device. The parameters of the signal are selected so that the tissue between the electrodes is subjected to short pulses of high intensity electric fields sufficient to cause electroporation of the cells of the tissue between the electrodes. The voltage is adjusted accurately so that the generated field has the desired, optimal amplitude. These fields make the walls of preselected cells in the tissue transiently permeable to permit the molecules to enter the preselected cells without killing the cells. The permeability results from the temporary formation of pores in the cell walls which are large enough to permit migration of the molecules through the cell walls.

Figure 4:
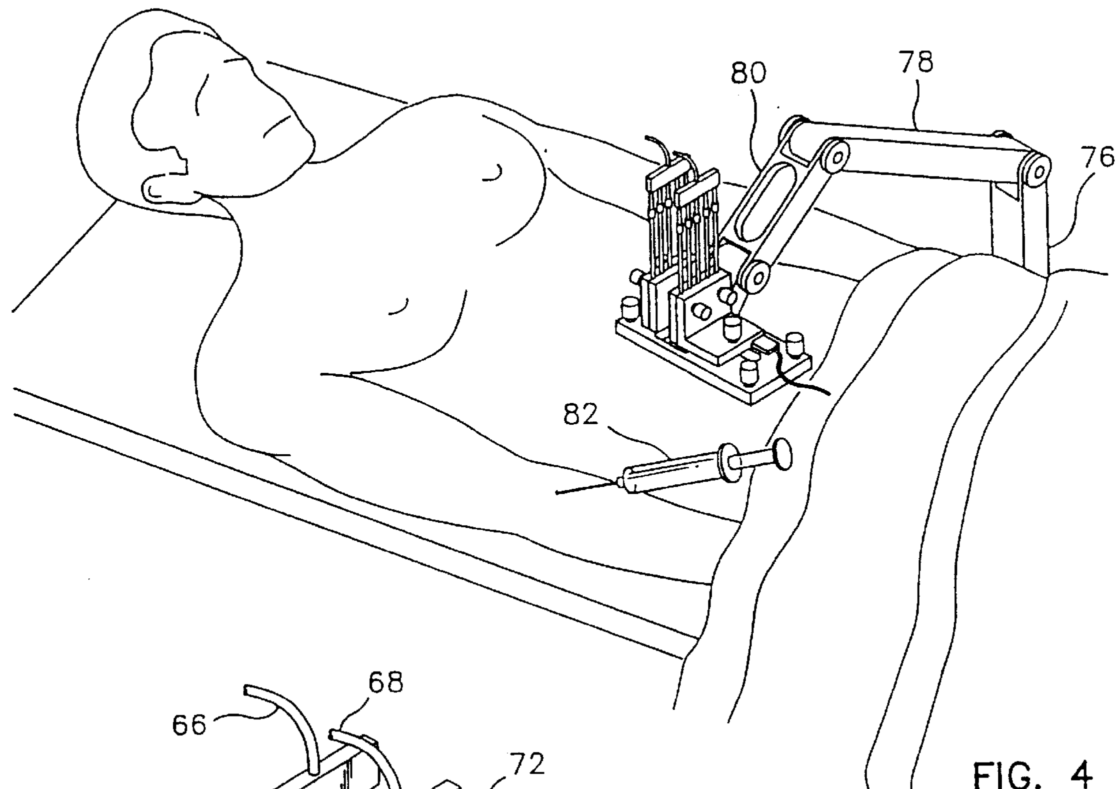
FIG. 4 is a view like FIG. 1 showing an alternate embodiment of electrodes.
Figure 5:
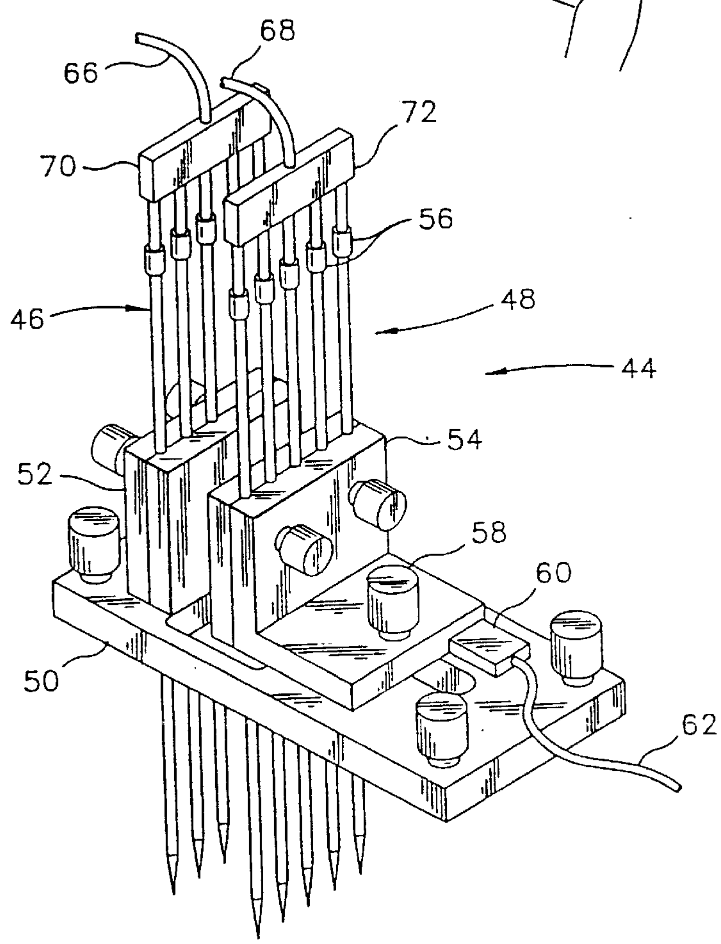
FIG. 5 is a detailed perspective view of the electrodes of FIG. 4.

An alternate embodiment of an electric field generating device is illustrated in FIGS. 4 and 5 and designated generally by the numeral 44. It includes a pair of spaced apart arrays of conductive needle electrodes 46 and 48 mounted on a dielectric carrier or support member 50. The needle array 46 is held in a fixed clamp which allows the needles to be adjusted in depth and also in distance from the array 46. The needles are each provided with a penetration stop 56. A gap spacing clamp 58 secures the clamp 54 in selected positions on the support 50. A gap spacing sensor 60 senses the distance between the needle arrays and generates a signal that is sent to the pulse generator via conductor cable 62. A pulse generator is connected to the needle electrodes by means of cables 66 and 68 with plugs 70 and 72.

In operation, a unit as above described is selected and mounted on suitable support such as a suitable clamp and articulated arm assembly as shown. A post 76 is clamped to the operating table and extends upward with arm 78 hinged to the post and arm 80 hinged on the outer end of arm 78. The support 50 is secured to the outer end of the arm 80. The support 50 is positioned over the patient and the needles of array 46 are inserted into one side of a selected tissue of a patient. The electrodes 48 are positioned at another side of the tissue to be treated and inserted into the tissue. Anticancer drugs are infused or injected into the patient by a syringe 82 or other suitable means. The drugs or other molecules may be injected into the blood stream or directly into the tumor or other tissue being treated.

The pulse generator connected to the electrodes is operated for repeatedly generating electric fields of a predetermined amplitude and duration in the tissue that lies between the electrodes. The fields are generated by applying a predetermined electric signal to the electrodes of the device. The distance between the electrodes is fed into the pulse generator as one parameter. The distance may be determined any number of ways and fed either manually or automatically into the generator.

Figure 6:
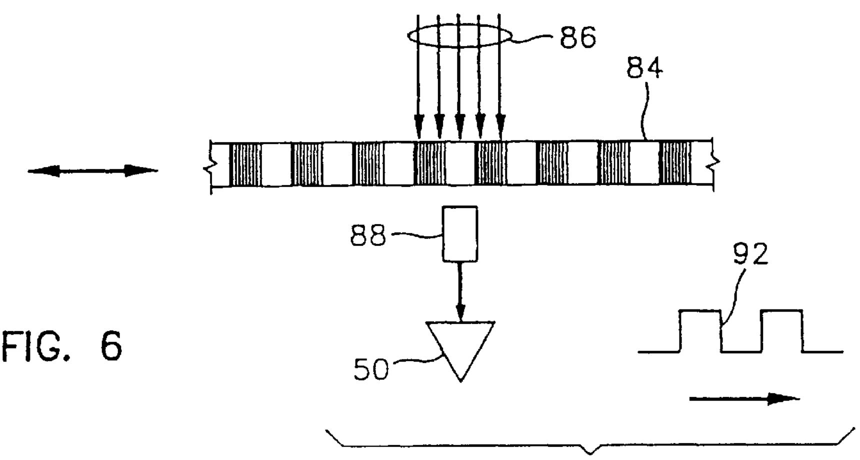
FIG. 6 is a diagrammatic illustration of the electrode position sensor.

Referring to FIG. 6, one example of a digital gap measurement system is illustrated. An optical raster strip 84 is attached to electrode support and moves with and in direct proportion to the electrode gap. The raster strip is disposed between a light source 86 and a light sensor 88 so that movement of the raster interrupts the light and generates a signal in the sensor 88 in proportion to the movement or position of the raster. The signal is amplified in an amplifier 90 and transmitted to the pulse generator which responds to set the output voltage for the generator to generate and transmit the required voltage pulses to the electrodes.

The function of the generator in the power pack 36 (FIG. 2) is to generate a predetermined electric signal which, when applied to the electrodes 24 and 26 results in applying electric fields of a predetermined amplitude and duration to the tissue that is clamped between the electrodes. Preferably these fields are applied repeatedly and their amplitude and duration optimized to make the walls of preselected cells in the tissue sufficiently permeable to permit the therapeutic molecules to enter the preselected cells.

Figure 7:
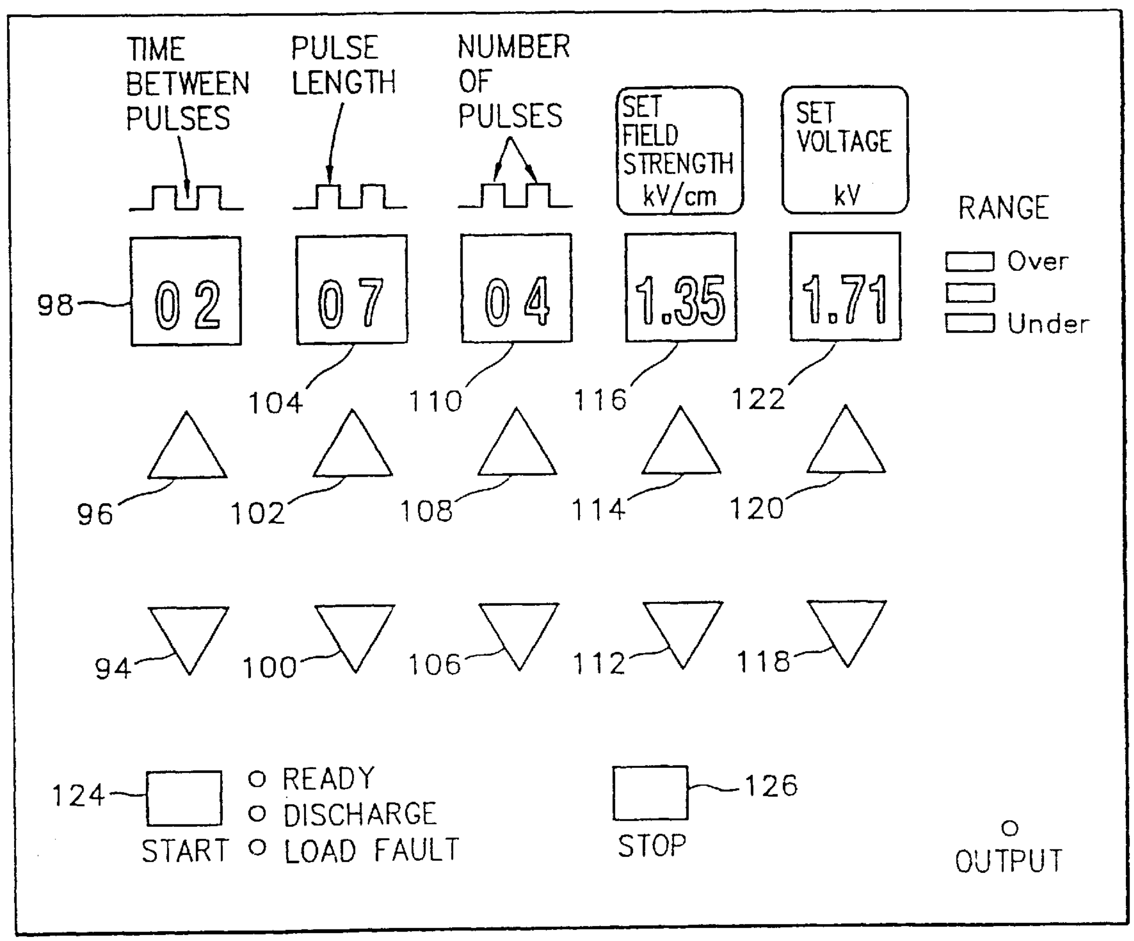
FIG. 7 is an illustration of the control panel for the power supply.

Referring to FIG. 7, one example of a control panel for a pulse power generator is illustrated. In the illustrated panel, the pulse parameters can be selectively adjusted by switches. The time between pulses can be selected downward by switch 94 and upward by switch 96 and read at readout 98. The pulse length can be selected downward by switch 100 and upward by switch 102 and read at 104. Switches 106 and 108 selectively decreases or increases the number of pulses which is read at 110. The field strength is selectively reduced at switch 112 and increased at switch 114 with the value indicated at 116. The voltage is set downwardly and upwardly by switches 118 and 120 respectively with the values read at 122. This voltage value will be determined by the distance between the electrodes (in cm) and by the set field strength in kV/cm at 116. Start and stop switches 124 and 126 enable starting and stopping the pulse generator.

Figure 8:
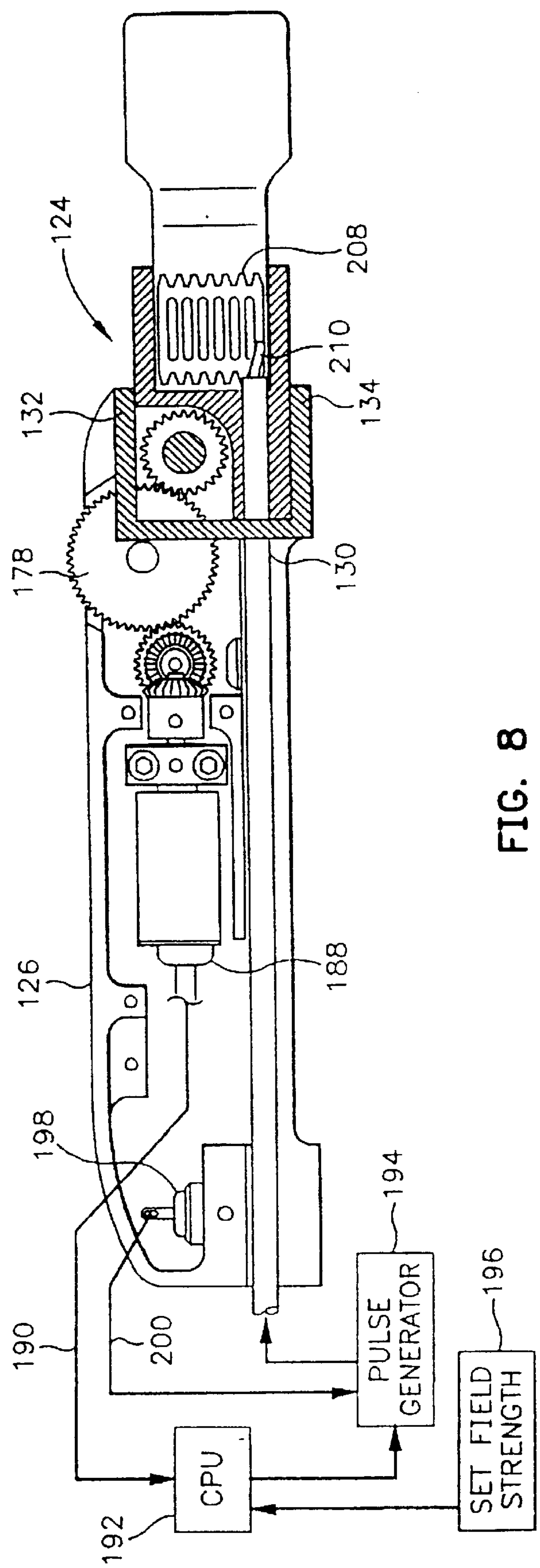
FIG. 8 is a side elevational view, partially in section, illustrating an alternate embodiment of the invention.
Figure 9:
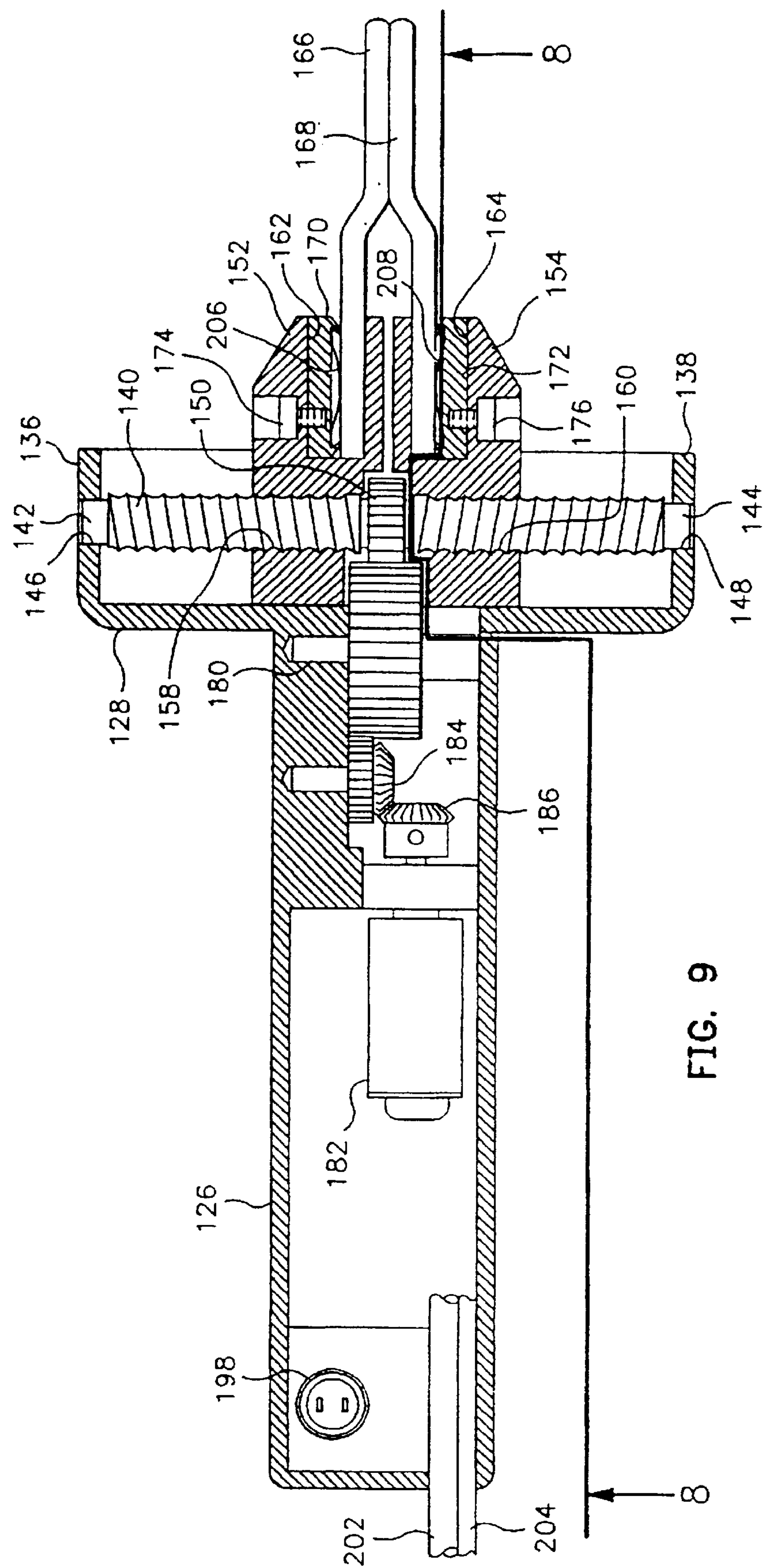
FIG. 9 is a top plan view, partially in section, of the embodiment of FIG. 8.

Referring to FIG. 8 and 9, a further embodiment of the invention is illustrated and designated generally by the numeral 124. The apparatus, as illustrated, comprises an elongated generally tubular housing 126, having a longitudinal axis and a transverse guide channel assembly at a forward or proximate end in which is adjustably mounted a pair of electrodes. The housing 126 may be constructed or formed of any suitable material, but preferably a suitable plastic nonconductive material and is formed with transverse housing portion 128. The housing 128 forms a generally rectangular box-like elongated guide channel formed of a back-wall 130, a top wall 132 and a bottom wall 134 enclosed at the ends by end walls 136 and 138.

A double helix screw 140 is rotatably mounted by suitable end journals 142 and 144 in bores 146 and 148, respectively, in the end walls 136 and 138. The double helical screw 140 has screw threads beginning at the center thereof and extending in opposite helicals toward the respective opposite ends thereof. The screw 140 has a pinion gear 150 formed or mounted at the center thereof. A pair of electrode mounting block or members 152 and 154 are mounting in the guide channel of the housing 128 and include respective threaded bores 158 and 160, threadably engaging the respective oppositely directed helical threads of the rotatable screw 140. The mounting blocks 152 and 154 are each formed with slots or receptacles 162 and 164 in which are detachably mounted a pair of electrodes 166 and 168. The electrodes 166 and 168 are detachably mounted within the sockets or slots 162 and 164 and are disposable. The electrodes are mounted such as by means of a pair of conductive contact spring plates 206 and 208 mounted in recesses in members 170 and 172 which are mounted in place such as by a pair of cap screws or the like 174 and 176.

A thumb wheel 178 includes gear teeth meshing with the gear teeth of gear 150 on screw 140 and projects upward beyond the top of the housing to enable manual rotation by a thumb or finger. The thumb wheel 178 is rotatably mounted on a suitable shaft 180 within the housing 126. The thumb wheel 178 also drivingly engages or couples to a potentiometer 182 through a gear train including gears 184 and 186. The potentiometer 182 is electrically connected by suitable conductors to an outlet connector 188 wherein a suitable cable such as a telephone wire may be plugged in and connected to a suitable signal responsive means such as a digital readout giving the space between the electrodes or connecting directly to a pulse power unit for providing the necessary input to adjust the voltage output proportional to the spacing between the electrodes.

In the illustrated embodiment, a cable 190 is connected to transmit a signal proportionate the electrode distance d to a microprocessor (CPU) 192 which controls a pulse generator 194. The microprocessor determines V from a preset field strength E (V/cm) input at 196 and the distance imputed from potentiometer 182. The CCPU then initiates charging of the capacitor bank of the signal generator to the voltage V. The operator activates the generator by closing a switch 198, and the generator delivers a pulse to the electrodes 166 and 168. The electrodes are connected to the pulse generator by a cable or cables 202 and 204 having a pair of conductors connected respectively to the electrodes via plates 170 and 172 and spring clips 206 and 208. In the illustrated embodiment the conductors (only one of which 210 is shown) are connected to conductive spring clips 206 and 208 in conductive engagement with electrodes in the sockets into which the disposable electrodes plug.

In operation, the hand-held caliper electrode assembly is grasped and positioned so that the electrodes 166 and 168 are touching (FIG. 9) to zero the instrument. The instrument is set such that the readout is zero for the electrodes touching and at their maximum distance representative of the maximum spacing between them. Intermediate these two positions a digital readout may be provided to show a numerical indication of the distance between the electrodes. The electrodes are manually adjusted to position to squeeze or engage opposite sides of a tumor or other body portion to be positioned there between. The electrodes are connected to a pulse generator as previously described, having the capability of applying a pulsed voltage of a selected amplitude. The distance between the electrodes is sensed by potentiometer 182 and fed to the CPU 192. It may also be noted on a readout and the distance entered into the pulse generator such that the generator is set to apply the desired voltage per unit distance between the electrodes. The pulse generator is then activated by closing switch 198 (e.g. by pushing a button not shown) to apply the predetermined voltage to the electrodes and thereby to the tumor or other body tissue.

In the illustrated embodiment the pulse generator 194 is provided with an interface such that the feedback signal defining the distance between the electrodes provides a signal that adjusts the voltage applied by the pulse generator to provide the desired field strength. This requires a simple circuit whereby the voltage represented by the resistance provided by the potentiometer 182 representing the distance between the electrodes is utilized by CPU 192 to set the voltage to be applied by the pulse generator 194.

An electric field across a cell membrane results in the creation of transient pores which are critical to the electroporation process. The pulse power generator provides the voltage (in kV) that travels across the tissue in the gap (in cm) between the electrodes 166 and 168. This potential difference defines what is called the electric field strength where E equals kV/cm. Each cell species has its own critical field strength for optimum electroporation. This is due to cell size, membrane make-up and individual characteristics of the cell wall itself. For example, some Gram positive bacteria are quite resistant to electroporation and require very high field strengths, i.e., greater than 17 kV/cm, before cell death and/or electroporation occurs. Generally, the required field strength varies inversely to the size of the cell. Mammalian cells require field strengths of typically 200 V/cm to several kV/cm.

The various parameters including electric field strengths required for the electroporation of any known cell is generally available from the many research papers reporting on the subject, as well as from a database maintained by Genetronics, Inc., San Diego, Calif., assignee of the subject application. The electric fields needed for in vivo cell electroporation, such as ECT, are similar in amplitude to the fields required for cells in vitro. These are in the range of from 100 V/cm to several kV/cm. This has been verified by the inventors own experiments and those of others reported in scientific publications. The first in vivo application of pulsed electric fields in the chemotherapy field to treat tumors was reported in 1987 by Okino in Japan.

The first set of planar experiments by Okino et al were conducted on Donryu rats in which carcinoma cells had been injected developing into tumors. Controlled studies were conducted in which they found the optimum conditions of treatment to be a field strength of 4–5 kV/cm and a pulse length of 3 ms to be applied thirty minutes after the systemic injection of the anticancer drug.

The most systematic study has been conducted by Mir and his colleagues at the Gustave-Roussy Institute in Paris. Mir et al first applied his mode of treatment to nude or conventional mice with subcutaneous transplanted tumors. The mice were treated by intramuscular injection of Bleomycin, followed by an application of short intense electric pulses to the tumor site. A control study was carried out in which 250 mgr of the drug was injected into both thighs and the electric field of 1.5 kV/cm, 8×100 msec pulses at one second intervals applied thirty minutes after Bleomycin injection. 35% were cured after this treatment with a field strength of between 1.2 and 1.5 kV/cm. Lower voltage resulted in fewer complete regressions, as well as more recurrences.

Mir et al conducted the first clinical trials with ECT in patients with head and neck squamous cell carcinoma and obtained encouraging results. The study involved seven patients with 32 nodules located in the anterior cervical region or upper part of the thorax. These were treated with Bleomycin 10 mg. per sqm which was given intravenously and electric pulses from a square wave generator applied 3.5 minutes after injection. The amount of drug used was less than 1/6 of the dose used in conventional chemotherapy with a field strengths of about 1.3 kV/cm. The pulses varied between 4 and 8 at one second intervals. The results were 9 partial regressions, 14 complete regressions, growth retarded in comparison to rapid increase in untreated nodules (two no change, and the results for three were not recorded).

The nature of the electric field to be generated is determined by the nature of the tissue, the size of the tumor and its location. It is desirable that the field be as homogenous as possible and of the correct amplitude. Excessive field strength results in lysing of cells, whereas a low field strength results in reduced efficacy.

The waveform of the electrical signal provided by the generator in the power pack 36 or 194 can be an exponentially decaying pulse, a square pulse, a unipolar oscillating pulse train or a bipolar oscillating pulse train. The electric field strength can be 0.2kV/cm to 20kV/cm. The pulse length can be ten $\mu$ to 100 ms. There can be one to one hundred pulses. Of course, the waveform, electric field strength and pulse duration are dependent upon the type of cells and the type of molecules that are to enter the cells via electroporation.

Pulse generators for carrying out the procedures described herein are and have been available on the market for a number of years. These can be easily modified to provide a suitable interface for signal input to set the voltage as described herein.

One suitable signal generator is the ELECTRO CELL MANIPULATOR Model ECM 600 commercially available from GENETRONICS, INC. of San Diego, Calif., U.S.A. The ECM 600 signal generator generates a pulse from the complete discharge of a capacitor which results in an exponentially decaying waveform. The electric signal generated by the ECM 600 signal generator is characterized by a fast rise time and an exponential tail. In the ECM 600 signal generator, the electroporation pulse length is set by selecting one of ten timing resistors marked R1 through R10. They are active in both High VM (capacitance fixed at fifty microfarads) and Low VM (with a capacitance range from 25 to 3,175 microfarads).

The ECM 600 signal generator has a knob that permits the adjustment of the amplitude of the set charging voltage applied to the internal capacitors from 50 to 500 volts in low VM and from 0.05 to 2.5 kV in the High VM. The amplitude of the electrical signal is shown on a display incorporated into the ECM 600 signal generator. This device further includes a plurality of push button switches for controlling pulse length, in the Low VM mode, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the flow-through chamber is an automatic cycle that takes less than five seconds. The manual button may be sequentially pressed to repeatedly apply the predetermined electric field.

While I have described preferred embodiments of my implantable electroporation method and apparatus for drug and gene delivery, it should be understood that modifications and adaptations thereof will occur to persons skilled in the art. Therefore, the protection afforded my invention should only be limited in accordance with the scope of the following claims.

I claim:

1. An apparatus for the therapeutic application of electroporation to a portion of the body of a patient, comprising:

an electrode assembly including a support member and a pair of adjustably spaced electrodes on said support member for adjustably positioning into engagement with and for generating an electric field at a preselected location within a body of a patient;

means for sensing and generating a distance signal proportionate to the space between said electrodes; and a pulse generator including means responsive to said distance signal for applying an electric signal to the electrodes proportionate to the space between said electrodes for repeatedly generating electric fields of a predetermined amplitude and duration for forcing the walls of preselected cells in the body portion to be transiently permeable for enabling molecules to enter said preselected cells.

2. An apparatus according to claim 1 wherein said electrode assembly comprise forceps having moveable clamping jaws defined by said spaced electrodes.

3. An apparatus according to claim 2 wherein the forceps are insertable through a tube.

4. An apparatus according to claim 3 wherein the forceps comprise a central shaft portion, said clamping jaws on one end of said shaft portion, a handle with actuating means on the other end, and said means for sensing the distance between said electrodes includes means for sensing the relative position of said actuating means.

5. An apparatus according to claim 1 wherein said electrode assembly comprises guide means supporting said electrodes for movement toward and away from one another, a rotating screw on said support member operatively connected for moving said electrodes, a manually operable wheel for rotating said screw and said means for sensing is a rheostat drivingly connected for rotating with said screw.

6. An apparatus according to claim 1 wherein the electric signal has a wave form selected from the group consisting of an exponentially decaying pulse, a square pulse, a unipolar oscillating pulse train and a bipolar oscillating pulse train.

7. An apparatus according to claim 1 wherein the electric field has a strength of between approximately 0.2 kV/cm and 20.0 kV/cm.

8. An apparatus according to claim 7 wherein each pulse has a duration of between approximately ten microseconds and one hundred milliseconds.

9. An apparatus according to claim 7 wherein the field applies between approximately one pulse and one hundred pulses to a given tissue volume.

10. An apparatus according to claim 1 wherein said electrodes detachably mount in sockets on said support means.

11. A method for the therapeutic application of electroporation to a portion of the body of a patient for introducing molecules into cells therein, comprising:

providing electrode means including adjustably spaced electrodes for generating an electric field at a preselected location within a body of a patient;

sensing the distance between said electrodes and generating a signal proportionate to the distance between said electrodes; and providing an electric pulse generator connected to said electrode means operating said pulse generator for applying an electric signal to said electrodes proportionate to the distance between said electrodes for causing said electrodes to repeatedly generate electric fields of a predetermined amplitude and duration thereby forcing the walls of preselected cells in the body portion to be transiently permeable for permitting the molecules to enter said preselected cells.

12. A method according to claim 11 wherein the electrode means are selected to comprise forceps having moveable clamping jaws defined by said spaced electrodes.

13. A method according to claim 12 wherein the forceps are insertable through a tube.

14. A method according to claim 13 wherein said forceps are selected to comprise a central shaft portion, said clamping jaws on one end of said shaft portion, a handle with actuating means on the other end, and said means for sensing the distance between said electrodes includes means for sensing the relative position of said actuating means.

15. A method according to claim 11 wherein said electrode assembly is selected to comprises guide means supporting said electrodes for movement toward and away from one another, a rotating screw on said support member operatively connected for moving said electrodes, a manually operable wheel for rotating said screw and said means for sensing is a rheostat drivingly connected for rotating with said screw.

16. A method according to claim 15 wherein said pulse generator is operated for generating an electric field having a strength of between approximately 0.2 kV/cm and 20 kV/cm.

17. A method according to claim 16 wherein said pulse generator is detected to generate an electric signal having a wave form selected from the group consisting of an exponentially decaying pulse, a square pulse, a unipolar oscillating pulse train and a bipolar oscillating pulse train.

18. A method according to claim 11 wherein said electrode means is selected to comprise a first plurality of needles mounted in a first clamp fixed on said holder and a second plurality of needles mounted in a second clamp movably mounted on said holder.

19. A method according to claim 18 wherein the electric signal has a wave form selected from the group consisting of an exponentially decaying pulse, a square pulse, a unipolar oscillating pulse train and a bipolar oscillating pulse train.

20. A method according to claim 19 wherein the electric field has a strength of between approximately 0.2 kV/cm and 20.0 kV/cm.

* * * * *